United States Patent
Vahala (10) Patent No.: US 9,993,196 B2
(45) Date of Patent: Jun. 12, 2018

(54) MAGNETIC RESONANCE MEASUREMENT OF ULTRASOUND PROPERTIES

(75) Inventor: Erkki Tapani Vahala, Hyvinkaa (FI)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 63 days.

(21) Appl. No.: 14/005,007

(22) PCT Filed: Mar. 12, 2012

(86) PCT No.: PCT/IB2012/051144
§ 371 (c)(1),
(2), (4) Date: Sep. 13, 2013

(87) PCT Pub. No.: WO2012/123880
PCT Pub. Date: Sep. 20, 2012

(65) Prior Publication Data
US 2013/0345547 A1  Dec. 26, 2013

(30) Foreign Application Priority Data

Mar. 17, 2011 (EP) ..................................... 11158681

(51) Int. Cl.
*A61B 5/00* (2006.01)
*G01R 33/48* (2006.01)
(Continued)

(52) U.S. Cl.
CPC ............ *A61B 5/4836* (2013.01); *A61B 5/055* (2013.01); *A61N 7/00* (2013.01); *A61N 7/02* (2013.01);
(Continued)

(58) Field of Classification Search
CPC ...... A61B 5/055; G01R 33/48; G01R 33/563; A61N 7/00
See application file for complete search history.

(56) References Cited

U.S. PATENT DOCUMENTS 5,276,397 A * 1/1994 Kawasaki .................. 324/309
6,128,522 A * 10/2000 Acker et al. ............... 600/411
(Continued)

FOREIGN PATENT DOCUMENTS

WO 2009137354 A1 11/2009
WO WO 2010122449 A1 * 10/2010 ............. B61K 5/055

OTHER PUBLICATIONS

Siegler, P. et al "Temperature Effect in High Intensity Focused Ultrasound Therapy Control using Dynamic MR Elastography", Proceedings of the International Society for Magnetic Resonance in Medicine, May 2005, p. 2363.

*Primary Examiner* — Tse Chen
*Assistant Examiner* — Joanne Hoffman (57) ABSTRACT

An apparatus (500, 600) comprising an ultrasound transducer element (300) for generating an ultrasonic beam (302) through a target zone (308, 538). The ultrasonic beam has an ultrasound frequency. The apparatus comprises a magnetic resonance system (502) with a resonant frequency modulator (542, 544, 516) for modulating a magnetic resonance frequency relative to a magnetic resonance of molecules in the target zone at the ultrasound frequency. Instructions cause a processor to repeatedly generate (100, 204) first gradient commands (562) which cause a magnetic field gradient coil to generate a first gradient magnetic field (710, 810) through the target zone. The gradient magnetic field has field lines directed in a first direction (304). The processor repeatedly modulates (102, 206) the magnetic resonance frequency at the ultrasound frequency, generates (104, 208) ultrasound commands (566), acquires (106, 210) magnetic resonance data from the target zone, and generates (108, 212) second gradient commands (564).

6 Claims, 6 Drawing Sheets

(51) Int. Cl.
   *G01R 33/563*   (2006.01)
   *A61N 7/02*   (2006.01)
   *A61B 5/055*   (2006.01)
   *A61N 7/00*   (2006.01)
   *A61B 90/00*   (2016.01)

(52) U.S. Cl.
   CPC ... *G01R 33/4808* (2013.01); *G01R 33/56358* (2013.01); *A61B 2090/374* (2016.02); *A61N 2007/0091* (2013.01); *A61N 2007/0095* (2013.01)

(56)  References Cited

U.S. PATENT DOCUMENTS

| | | | |
|---|---|---|---|
| 6,246,895 B1* | 6/2001 | Plewes | A61B 8/00 324/309 |
| 6,252,399 B1* | 6/2001 | Pruessmann et al. | 324/307 |
| 6,613,004 B1* | 9/2003 | Vitek et al. | 601/2 |
| 2004/0035182 A1* | 2/2004 | Kadlecek | 73/23.2 |
| 2004/0039280 A1* | 2/2004 | Wu | G01R 33/4804 600/412 |
| 2004/0162483 A1* | 8/2004 | Kimura | G01R 33/56308 600/419 |
| 2005/0228275 A1* | 10/2005 | Kawashima | A61B 8/12 600/437 |
| 2006/0293598 A1 | 12/2006 | Fraser | |
| 2007/0167806 A1* | 7/2007 | Wood et al. | 600/459 |
| 2008/0200795 A1* | 8/2008 | Steckner | 600/411 |
| 2009/0062724 A1* | 3/2009 | Chen | 604/22 |
| 2009/0131782 A1 | 5/2009 | Moonen | |
| 2009/0230966 A1* | 9/2009 | Ehnholm | G01R 33/3415 324/322 |
| 2009/0253979 A1 | 10/2009 | Ehman | |
| 2010/0010595 A1* | 1/2010 | Bruggers | 607/96 |
| 2010/0026298 A1 | 2/2010 | Wald | |
| 2010/0106005 A1 | 4/2010 | Karezmar | |
| 2010/0106078 A1* | 4/2010 | Dimitrova et al. | 604/22 |

* cited by examiner

MAGNETIC RESONANCE MEASUREMENT OF ULTRASOUND PROPERTIES

CROSS-REFERENCE TO PRIOR APPLICATIONS

This application is the U.S. National Phase application under 35 U.S.C. § 371 of International Application No. PCT/IB/2012/051144, filed on Mar. 12, 2012, which claims the benefit of European Patent Application No. 11158681.4, filed on Mar. 17, 2011. These applications are hereby incorporated by reference herein.

TECHNICAL FIELD

The invention relates to high intensity focused ultrasound, in particular to magnetic resonance guided high intensity focused ultrasound.

BACKGROUND OF THE INVENTION

Ultrasound from a focused ultrasonic transducer can be used to selectively treat regions within the interior of the body. Ultrasonic waves are transmitted as high energy mechanical vibrations. These vibrations induce tissue heating as they are damped, and they can also lead to cavitation. Both tissue heating and cavitation can be used to destroy tissue in a clinical setting. However, heating tissue with ultrasound is easier to control than cavitation. Ultrasonic treatments can be used to ablate tissue and to kill regions of cancer cells selectively. This technique has been applied to the treatment of uterine fibroids, and has reduced the need for hysterectomy procedures. At lower powers or in pulsed mode, ultrasound can be used to selectively deliver genetic material or medicine to a region.

To perform ultrasonic therapy, a focused ultrasonic transducer can be used to focus the ultrasound on a particular treatment volume. The transducer is typically mounted within a medium, such as degassed water, that is able to transmit ultrasound. Actuators are then used to adjust the position of the ultrasonic transducer and thereby adjust the tissue region that is being treated. In focused ultrasound, ultrasound from several ultrasound transducer elements are used to create constructive interference in at a sonication point or target zone. The position of the sonication point can be electronically steered by controlling the phase of ultrasound emitted by each of the ultrasonic transducer elements.

SUMMARY OF THE INVENTION

The invention provides for an apparatus, a method, and a computer program product in the independent claims. Embodiments are given in the dependent claims.

A difficulty of performing ultrasonic therapy is that the effect of tissues on the between the target zone and the ultrasonic transducer on the phase of the ultrasound may not be known. This may cause a defocusing of the sonication point or even a shift in the location of the sonication point. This is because the multiple ultrasonic beams add constructively in a different location than was anticipated. Embodiments of the invention may solve these and others by providing a means of directly measuring the phase of ultrasound in a target zone using magnetic resonance imaging.

The abstract 'Temperature effect in high intensity focused ultrasound therapy control using dynamic MR elastography' by P. Siegler et al. in ISMRM 2005 (2363) mentions that high-intensity focused ultrasound lesions have a decreased elasticity and these can be measured using MR elastography. The US-patent application US2010/026298 mentions that a magnetic resonance guided FUS ("MRgFUS") treatment plan can be updated by imaging the location and extent of a mechanical wave field produced in a subject by an ultrasound transducer at low power. A spin-lock radiofrequency pulse, having a resonance frequency matched to that of the induced oscillatory motion, is applied to the subject.

Means to measure accurate ultrasound wave phase and amplitude values in target tissue is needed for calibrating High-Intensity Focused Ultrasound (HIFU) devices to produce sharply delineated necrotic volumes. In addition, measured amplitude values provide valuable clinical information about the target tissue properties, similarly to Magnetic Resonance Elastography. The current state of the art utilizes macroscopic shear waves for such purposes. The invention may provide for a method where a high frequency ultrasound wave is measured directly with Magnetic Resonance Imager.

The state of the art in High-Intensity Focused Ultrasound (HIFU) temperature imaging utilizes the macroscopic shifts in tissue caused by the radiation force impulses of relatively low-frequency, periodic transmissions of ultrasound energy. The tissue shifts elicit information about tissue elasticity and intensity of the ultrasound. The ultrasound phases can be optimized by adjusting the phases until the tissue shift at the wanted volume is at maximum. Acoustic Radiation Force Impulse (ARFI) imaging is similarly an imaging method where the macroscopic tissue displacement is used to encode an image, whose contrast is affected by the acoustic properties of the tissue.

Acoustic radiation force displacement based methods cannot produce direct phase information, as the phenomenon is caused by the transformation of coherent wave energy into macroscopic momentum of tissue. In multipath ultrasound transmissions the lack of phase information becomes a problem as phase optimization becomes a lengthier and more complex process.

In Elastography, the measured amplitude is that of the macroscopic tissue and not the microscopic pressure wave movement.

The invention may provide for a method where the pressure wave properties, such as the phase, direction, and amplitude of the wave can be determined with sub millimeter accuracy.

In addition to normal magnetic resonance (MR) imaging or measurement methods, a strong magnetic resonance (MR) gradient field is placed along the direction of interest in the presence of ultrasound energy transmission. Magnetic Resonance Radio-Frequency (RF) transmission is started. The RF frequencies are modulated with ultrasound frequency to purposefully excite and measure only those particles that experience wave motion in the direction of interest at the ultrasound frequency. The excited particles are then measured using state of the art MR techniques.

The measured MR signal is a function of the phase coherence of ultrasound at the local tissue and at the RF transmission, which can be used for determining the phase of the ultrasound at tissue.

Varying the direction of interest maps the oscillating particle movement component in each direction.

The amplitude of particle oscillation along the direction of interest corresponds to the amplitude of the RF frequency modulation, which allows decoding of the amplitude from the MR signal.

In one of the embodiments, a High Intensity Focused Ultrasound (HIFU) device is used for producing pulses of ultrasound energy. An MR volume is excited. A strong "diffusion" gradient field of an MR scanner is placed along the estimated transmission path to measure the longitudinal oscillation of the pressure wave. A long RF pulse, modulated at ultrasound frequency, is applied to invert the magnetization vector in a subvolume of the initially excited volume. If the phase and amplitude of the ultrasound movement in the excited volume does not match that of the modulating RF frequency, a non-complete inversion occurs. A dephasing gradient can be used to destroy out-of-phase magnetization. State of the art MR techniques can be used to recover the phase coherence and measure the remaining magnetization. Comparison with normally excited MR volume and varying the RF modulation/ultrasound phase and/or amplitude elicits the necessary data for determining the phase and amplitude of the longitudinal pressure wave in the volume.

In one of the embodiments, instead of an RF pulse, a steady state is established with modulated continuous wave RF before the signal is recovered and excited via state-of-the-art MR methods.

In one of the embodiments, instead of a single modulated RF frequency, a multi-frequency bandwidth, of known phase behavior and covering the typical oscillating wave amplitudes, is modulated to excite particles regardless of the amplitude.

The invention is of direct relevance to the HIFU development. The invention can also be used for clinical, diagnostic imaging. The invention can also be used for NMR microscopy. The invention provides for an apparatus, a method of operating an apparatus, and a computer product in the independent claims. Embodiments are given in the dependent claims.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'computing device' as used herein encompasses to any device comprising a processor. A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for an apparatus comprising an ultrasound transducer element for generating an ultrasonic beam through a target zone of a subject. The ultrasonic transducer element may for instance be a piezoelectric or other transducer which vibrates at ultrasonic frequencies and generates ultrasonic energy resulting in the ultrasonic beam. In some embodiments the ultrasonic transducer element may be one of many ultrasound transducer elements. The ultrasonic beam has an ultrasound frequency. The ultrasound frequency is the frequency at which the ultrasound beam is propagating through the subject. The ultrasonic beam is directed in a first direction through the target zone.

The apparatus further comprises a magnetic resonance system for acquiring magnetic resonance data from a data acquisition zone. In some embodiments the magnetic resonance system may be a magnetic resonance imaging system. In other embodiments the magnetic resonance system may be a particular magnetic resonance spectrometer. The target zone is within the data acquisition zone. The magnetic resonance system comprises a resonant frequency modulator for modulating a magnetic resonance frequency relative to a nominal magnetic resonance of molecules in the target zone. The magnetic resonance of the molecules or the nominal magnetic resonance of the molecules in the target zone is the Larmor frequence of the molecules in the target zone when the ultrasound beam is not passing through the target zone and the resonance frequency modulator is not modulating the magnetic resonance frequency. The resonant frequency modulator is adapted for modulating the magnetic resonance frequency at the ultrasound frequency. The magnetic resonance system further comprises a magnetic field gradient coil. The magnetic field gradient coil may be adapted for generating magnetic fields through the target zone.

In one embodiment, the resonant frequency modulator is able to change the resonant frequency of magnetic spins within the target zone. This may be accomplished, for instance, by using a magnetic resonance imaging system which comprises a magnet which is adapted for using a coil for changing the B0 field at the ultrasound frequency. In another embodiment, the magnetic resonance system may also comprise a radio-frequency system for generating radio-frequency energy which is used to manipulate the orientations of spins within the target zone or even within the data acquisition zone. The radio-frequency may be also modulated at the ultrasound frequency. As the resonant frequency of the molecules in the target zone changes, the frequency of the radio-frequency energy changes also.

The resonant frequency modulator has several effects. First it modulates or changes the magnetic resonance frequency. The amount by which the frequency is changed is referred to as the magnitude. This may also be alternatively referred to as the amplitude, but the use of amplitude when speaking of frequency modulation may be confusing so magnitude is used instead. When it is stated that the resonant frequency modulator is adapted for modulating the magnetic resonance frequency at the ultrasound frequency, another way of stating this is: instantaneous magnetic resonance frequency deviation from the nominal value is locked with a factor of proportionality to the instantaneous value of the ultrasound amplitude and hence varies at the ultrasound frequency. So there is thus a frequency in how fast the resonant frequency changes and also the magnitude or amplitude of how much it changes.

The apparatus further comprises a processor for controlling the apparatus. The apparatus further comprises a memory containing machine executable instructions. Execution of the machine executable instructions causes the processor to repeatedly generate first gradient commands which cause the magnetic field gradient coil to generate a first gradient magnetic field through the target zone. The gradient magnetic field has field lines directed in a first direction. The field lines define a gradient direction for the magnetic field. For instance, if the field lines are parallel to a direction then the gradient direction is also parallel to the first direction. Execution of the instructions further causes the processor to repeatedly modulate a magnetic resonance frequency relative to a magnetic resonance of molecules in the target zone at the ultrasound frequency during application of the first gradient magnetic field. The processor may use resonant frequency modulator to modulate the resonant frequency.

The instructions may also contain commands to send the first gradient commands to the magnetic resonance imaging system. Execution of the instructions further causes the processor to repeatedly generate ultrasound commands which cause the ultrasound transducer to generate ultrasound during the application of the first gradient magnetic field. Execution of the instructions may also cause the processor to repeatedly send the ultrasound commands to the ultrasound transducer element. In some embodiments the apparatus may comprise an ultrasound system. The ultrasound system may comprise the ultrasound transducer element and a power supply adapted for supplying the ultrasound transducer element with alternating current power at the ultrasound frequency.

Execution of the instructions further causes the processor to repeatedly acquire magnetic resonance data from the target zone. For instance the processor may send instructions to the magnetic resonance imaging system which cause it to acquire the magnetic resonance data. In some embodiments execution of the instructions may cause the processor to receive the magnetic resonance data from the magnetic resonance imaging system. Execution of the instructions further cause the processor to repeatedly generate second gradient commands which cause the magnetic field gradient coil to generate a second gradient magnetic field through the target zone prior to the acquisition of the magnetic resonance data. This second gradient magnetic field is essentially a refocusing gradient. The first gradient magnetic field was a magnetic field gradient that was performed during excitation of the spins in the target zone. The second gradient magnetic field has a polarity opposite to the first gradient magnetic field.

Embodiments of the invention may be advantageous because the magnetic resonance data comprises data which is descriptive of properties of the ultrasonic beam which is traveling through the target zone. This data may be analyzed for diagnostic purposes and it may also be used directly for analytical purposes.

In another embodiment the resonant frequency modulator is further adapted for controlling the phase of modulation relative to the ultrasonic beam. Execution of the instructions further causes the processor to generate a set of phases. Execution of the instructions further cause the processor to modulate the magnetic resonance frequency of molecules in the target zone at the ultrasound frequency using each of the set of phases during repeated application of the first gradient magnetic field. Execution of the instructions further causes the processor to determine the magnetic resonance signal from the target zone for each of the set of phases.

Execution of the instructions further causes the processor to determine a phase using the set of phases which maximize the magnetic resonance signal in the target zone. The phase may be determined in several different ways. For instance the individual phase which gives the largest signal may be selected. In other embodiments a curve may be fit to the signal strength corresponding to each of the set of phases. In this case the phase could be determined from the curve fit. In yet other embodiments a model may be fit to the set of phases. The model may then be used to predict the phase. Execution of the instructions further causes the processor to store the phase in the memory.

In another embodiment the resonant frequency modulator is further adapted for controlling the magnitude of the frequency modulation. The magnitude as used herein is descriptive of the change in frequency of the nominal frequency of magnetic spins within the target zone. The term amplitude may also be used interchangeably with magnitude. Execution of the instructions further causes the processor to generate a set of frequency modulation magnitudes. Execution of the instructions further cause the processor to modulate the magnetic resonance frequency molecules in the target zone at the ultrasound frequency using each of the set of frequency modulation magnitudes during repeated application of the first gradient magnetic field. Execution of the instructions further causes the processor to determine the magnetic resonance signal from the target zone for each of the set of frequency modulation magnitudes. Execution of the instructions further cause the processor to determine a maximum magnitude using the set of frequency modulation magnitudes which cause a large magnetic resonance signal in the target zone. Again this maximizing magnitude may be determined in several different ways. For instance the frequency modulation magnitude which causes the largest signal may be selected. In other embodiments a curve may be fit to the signals or a model may be used as was described previously. Execution of the instructions further causes the processor to store the maximizing magnitude in the memory.

In another embodiment execution of the instructions further cause the processor to calculate an ultrasound amplitude for the target zone using the maximizing magnitude. The ultrasound amplitude may be calculated because the strength of the first gradient magnetic field is a known quantity. The maximizing magnitude has been measured. The maximizing magnitude can be translated into a magnetic field strength by calculating the Larmor frequency. The change in the magnetic field which the molecules experience is then a known quantity since the strength of the first gradient magnetic field is known the placement corresponding to the known change in the magnetic field that the molecule experiences may be directly translated into the ultrasound amplitude in the target zone.

In another embodiment execution of the instructions further cause the processor to generate a set of directions. Execution of the instructions further cause the processor to modulate the nominal magnetic resonance frequency of the molecules in the target zone at the ultrasound frequency using each of the set of directions during repeated application of the gradient magnetic field. Execution of the instructions further causes the processor to determine the magnetic resonance signal from the target zone for each of the set of directions. Execution of the instructions further causes the processor to determine a first direction using the set of directions which maximizes the largest magnetic resonance signal in the target zone. For instance the first direction may be selected from the set of directions which cause the largest magnetic resonance signal in the target zone. In other embodiments a curve or a model may be used to determine the direction which maximizes the signal. This direction which maximizes the signal is then the first direction. Execution of the instructions further causes the processor to store the direction in the memory. This embodiment of the invention may be beneficial because the direction in which the ultrasound beam travels may be determined empirically.

In another embodiment the first direction is aligned with the direction of travel of the ultrasonic beam.

In another embodiment the magnetic resonance system further comprises a transceiver system adapted for connecting a radio-frequency antenna for acquiring the magnetic resonance data.

In another embodiment the transceiver system is adapted for modulating the frequency and/or phase of radio-frequency power generated by the transceiver relative to the proton resonance frequency of atomic spins within the target zone at the ultrasound frequency. The transceiver is the resonance frequency modulator.

In another embodiment the magnetic resonance system further comprises a B0 field modulation coil. In some embodiments the B0 field modulation coil may be the magnet for the magnetic resonance imaging system. In other embodiments the B0 field modulation coil is an additional coil installed into the magnet which is used to modulate the B0 field. The magnetic resonance system further comprises a B0 field modulation power supply for supplying the B0 field modulation coil with current. The B0 field modulation power supply is adapted for modulating the current supplied to the B0 field modulation coil at the ultrasound frequency. The resonant frequency modulator comprises the B0 field modulation coil and the B0 field modulation power supply. The amount and phase of the current supplied to the B0 field modulation coil by the B0 field modulation power supply is able to know the magnitude and phase offset of the frequency modulation.

In both the previous two aforementioned embodiments components such as a phase lock loop may be used to control the phase of the radio-frequency power or the alternating current supplied by the B0 field modulation power supply relative to the phase of the ultrasonic beam.

In another embodiment the magnetic resonance system is a magnetic resonance imaging system.

In another embodiment the data acquisition zone is a cell.

In another embodiment the data acquisition zone is a volume.

In another embodiment the data acquisition zone is a slice.

In another embodiment the medical apparatus further comprises a high-intensity focused ultrasound system. The high-intensity focused ultrasound system comprises an ultrasound transducer for sonicating the target zone. The ultrasound transducer comprises the ultrasound transducer element.

In another embodiment the apparatus further comprises an ultrasound transducer power supply for supplying alternating current electrical power to the ultrasound transducer.

In another embodiment the ultrasound transducer comprises multiple ultrasound transducer elements. Execution of the instructions further causes the processor to calculate a set of control phases to sonicate the target zone. The set of control phases define the phase of alternating current supplied to each of the multiple ultrasound transducer elements. Execution of the instructions further causes the processor to generate sonication commands using the set of phases. The sonication commands cause the high-intensity focused ultrasound system to sonicate the target zone. The sonication commands are the ultrasound commands. Execution of the instructions further cause the processor to send the sonication commands to the high-intensity focused ultrasound system. Execution of the instructions further cause the processor to calculate a set of corrected phases in accordance with the repeatedly acquired magnetic resonance data. In this embodiment the direction, phase, and/or magnitude of the ultrasound in the target zone may be determined and used to calculate a set of corrected phases. This may be extremely advantageous for correctly focusing a high-intensity focused ultrasound system to sonicate the target zone properly.

In another embodiment the medical apparatus is a nuclear magnetic resonance spectrometer. In this embodiment the subject may be a sample of summary agent or a tissue sample inserted into the nuclear magnetic resonance spectrometer.

In another aspect the invention provides for a method of operating the apparatus. Likewise the invention also provides for a computer-implemented method of operating an apparatus. The apparatus comprises an ultrasound transducer element for generating an ultrasonic beam through a target zone of a subject. The ultrasonic beam has an ultrasound frequency. The apparatus further comprises a magnetic resonance system for acquiring magnetic resonance data from a data acquisition zone. The target zone is within the data acquisition zone. The magnetic resonance system comprises a resonant frequency modulator for modulating a magnetic resonance frequency relative to a magnetic resonant frequency of molecules in the target zone by the ultrasound frequency.

The magnetic resonance system further comprises a magnetic field gradient coil. The method comprises repeatedly performing the step of generating first gradient commands which cause the magnetic field gradient coil to generate a first gradient magnetic field through the target zone. The gradient magnetic field has field lines directed in a first direction. The method further comprises repeatedly performing the step of modulating the magnetic resonance frequency at the ultrasound frequency during the application of the first gradient magnetic field. The method further comprises repeatedly performing the step of generating ultrasound commands which cause the ultrasound transducer to generate ultrasound during the application of the first gradient magnetic field. The method further comprises repeatedly performing the step of acquiring magnetic resonance data from the target zone. The method further comprises repeatedly performing the step of generating second gradient commands which cause the magnetic field gradient coil to generate a second gradient magnetic field through the target zone prior to the acquisition of the magnetic resonance data. The second gradient magnetic field has a polarity opposite to the gradient magnetic field.

In another aspect the invention provides for a computer program product comprising machine executable instructions for execution by a processor of an apparatus. The machine executable instructions may for instance for stored on a computer-readable storage medium. The apparatus comprises an ultrasound transducer element for generating an ultrasonic beam through a target zone of a subject. The ultrasonic beam has an ultrasound frequency. The apparatus further comprises a magnetic resonance system for acquiring magnetic resonance data from a data acquisition zone. The target zone is within the data acquisition zone. The magnetic resonance system comprises a resonant frequency modulator for modulating a nominal magnetic resonance frequency relative to a magnetic resonance of molecules in the target zone by the ultrasound frequency. The magnetic resonance system further comprises a magnetic field gradient coil.

Execution of the instructions cause the processor to repeatedly generate first gradient commands which cause the magnetic field gradient coil to generate a first gradient magnetic field through the target zone. The gradient magnetic field has field lines directed in a first direction. Execution of the instructions further causes the processor to repeatedly modulate the nominal magnetic resonance frequency at the ultrasound frequency during the application of the first gradient magnetic field. Execution of the instructions further cause the processor to repeatedly generate ultrasound commands which cause the ultrasound transducer to generate ultrasound during the application of the first gradient magnetic field. Execution of the instructions further causes the processor to repeatedly acquire magnetic resonance data from the target zone. Execution of the instructions further cause the processor to repeatedly generate second gradient commands which cause the magnetic field gradient coil to generate a second gradient magnetic field through the target zone prior to the acquisition of the magnetic resonance data. The second gradient magnetic field has a polarity opposite to the first gradient magnetic field.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
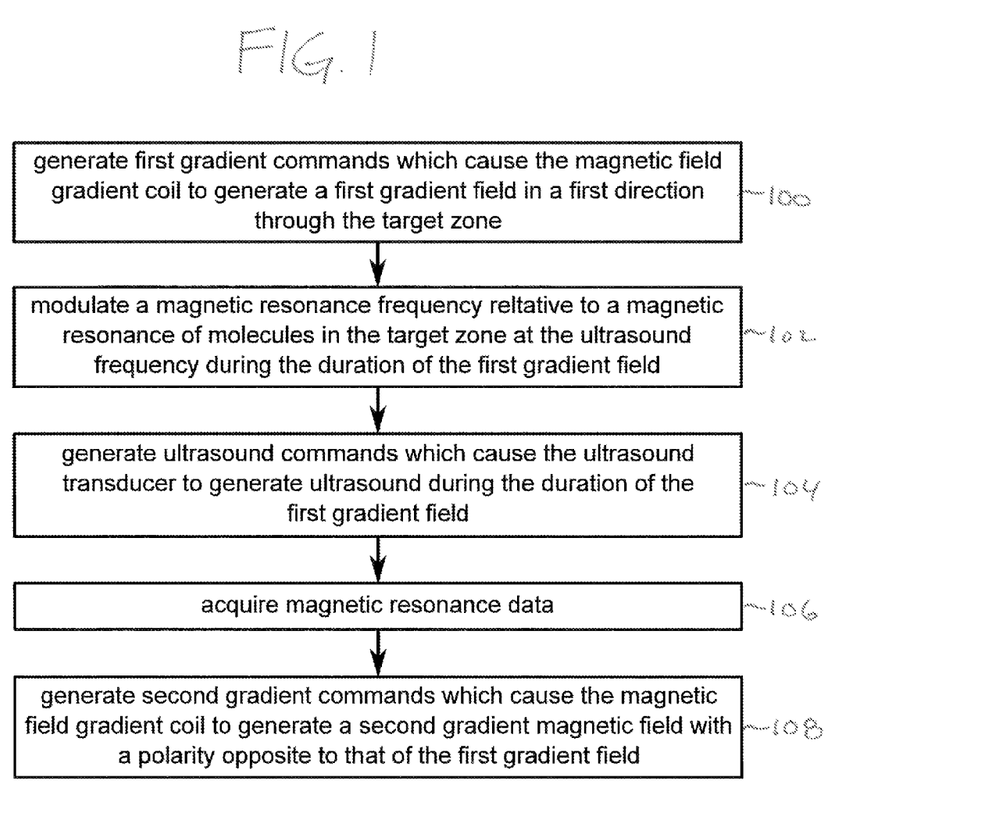
FIG. 1 shows a flow diagram which illustrates a method according to an embodiment of the invention.

FIG. 1 shows a flow diagram which illustrates a method according to an embodiment of the invention. In step 100 first gradient commands are generated which cause the magnetic field gradient coil to generate a first gradient field in a first direction through the target zone. Next in step 102 a magnetic resonance frequency is modulated relative to magnetic resonance molecules in the target zone at the ultrasound frequency during the duration of the first gradient. Next in step 104 ultrasound commands are generated which cause the ultrasound transducer to generate ultrasound during the duration of the first gradient field. In step 106 magnetic resonance data acquisition starts from a magnetic resonance imaging system. Finally in step 108 second gradient commands are generated which cause the magnetic field gradient coil to generate a second gradient magnetic field with a polarity opposite to that of the first gradient field.

Figure 2:
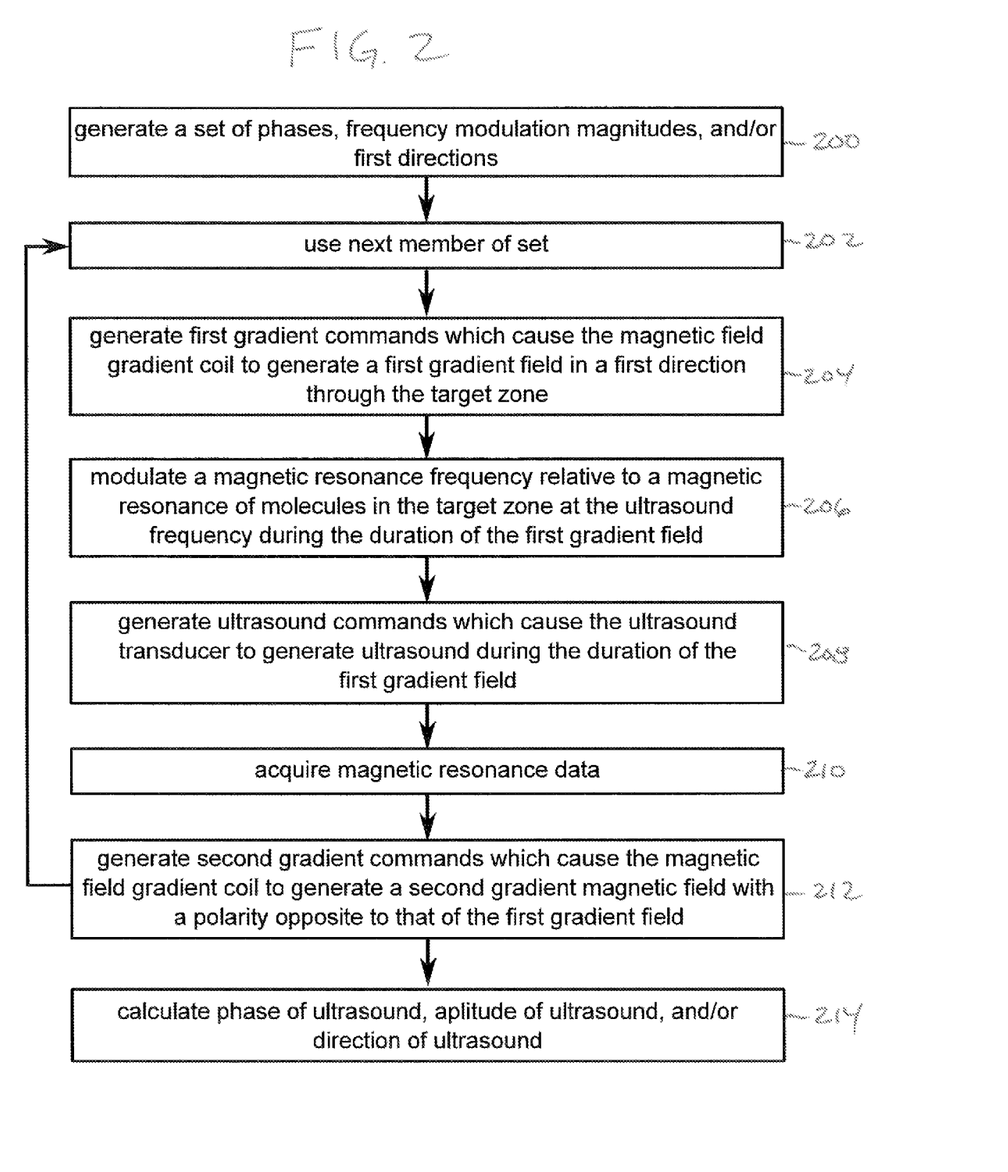
FIG. 2 shows a flow diagram which illustrates a method according to a further embodiment of the invention.

FIG. 2 shows a flow diagram which illustrates a method according to a further embodiment of the invention. In step 200 a set of phases, frequency modulation magnitudes, and/or first directions is generated. Next in step 202 the first or the next member of the set if used. In step 204 the first gradient commands are generated which cause the magnetic field gradient coil to generate a first gradient field in a first direction through the target zone. In step 206 a magnetic resonance frequency of a magnetic resonance of molecules in the target zone is modulated at the ultrasound frequency during the duration of the first gradient field. In step 208 ultrasound commands are generated which cause the ultrasound transducer to generate ultrasound during the duration of the first gradient field. Next in step 210 magnetic resonance data acquisition is started using the magnetic resonance imaging system. In step 212 second gradient commands are generated which cause the magnetic field gradient coil to generate a second gradient magnetic field with a polarity opposite to that of the first gradient field. After step 212 step 202 is performed and the next member of the set is used. Steps 202-212 are repeated until all members of the set have been used. Finally in step 214 the phase of the ultrasound, the amplitude of the ultrasound, and/or the direction of the ultrasound is calculated using the acquired magnetic resonance data.

When the ultrasound pressure moves back and forth the molecules along a strong gradient field, the instantaneous precession frequency of the spins changes as a function of their displacement; the frequency rises above the base, then sinks below in a repeating sinusoidal pattern. If the frequency of the B1 transmit pulse is altered in-sync with the displacement, the spins see a perfectly transversal B1 pulse. If the frequency is altered too much, even with a perfectly phase-locked system, the system overshoots and the effect is worst at the peak displacement offsets: instead of a perfect transversal pulse, there is a frequency difference between the instantaneous frequency of the transmit pulse and the Larmor frequency experienced by the spins, so the B1 is not fully transversal anymore, leading to a different excitation behavior (e.g., in a simplest case the non-perfect B1 pulse can be used to detect a FID with signal loss). Similarly, with too small a deviation, the system under-shoots: therefore the signal is at maximum when we have selected a maximum frequency deviation that matches the maximum displacement.

The instantaneous frequency shift is proportional to the product of the amplitude of the gradient projected along the ultrasound displacement and the ultrasound displacement itself. For example, the vibrating tissue may change its frequency from 41999996.0 Hz to 42000004.0 Hz twice per 0.7 us if the ultrasound (US) frequency is 1.4 MHz. If we shift the RF frequency, in phase with the vibration and with the same amount, at the US frequency, then, from the reference frame of vibrating molecules, the B0 does not seem to change at all—the effect of the gradient is negated, whereas non-vibrating tissue sees the varying RF frequency: the effect is the same as if the B0 would vary by 0.1 uT at the US frequency.

In determining the amplitude, the amplitude of the maximal shift of the RF frequency can be changed in small steps. When the received signal is at maximum, the RF shift is equal to the tissue displacement due to the vibration.

Figure 3:
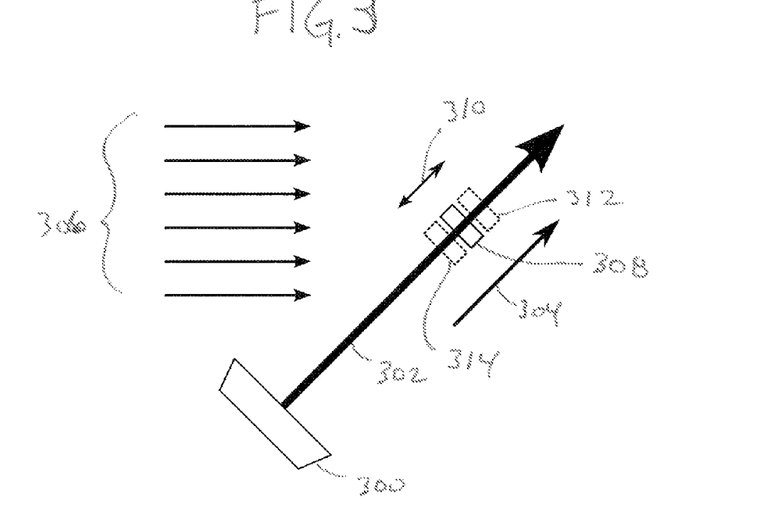
FIG. 3 shows a diagram which is an aid to understanding functioning of embodiments of the invention.

FIG. 3 shows a diagram which is an aid to understanding functioning of embodiments of the invention. In this Fig. there is an ultrasound transceiver element 300 shown. The ultrasound transceiver element 300 generates an ultrasonic beam 302 which passes through a target zone 308. The arrows labeled 306 indicate the direction of field lines of the B0 field. The arrow 304 indicates the first direction which also indicates the direction of the field line for the first gradient magnetic field. The first direction in this example is a line with the direction of travel of the ultrasound beam 302. As the ultrasound 302 travels through the target zone 308 the ultrasound causes the target zone 308 to move back and forth along the direction of travel 310. The target zone 308 moves into a first position 312 and a second position 314 and all positions in between. As the target zone 308 travels along the direction of the first direction 304 the gradient magnetic field causes the resonant frequency magnetic spins in the target zone 308 to change as it travels between the first position 312 and the second position 314.

Figure 4:
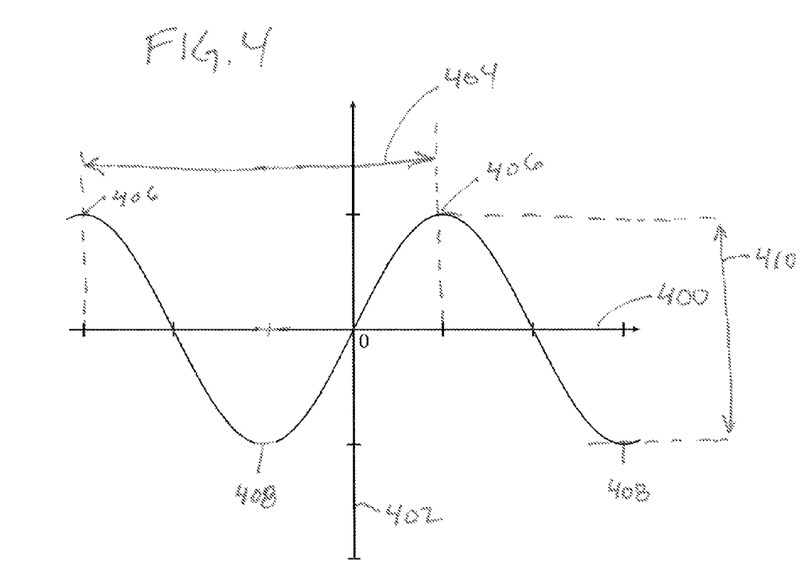
FIG. 4 shows a plot of the resonant frequency of the target zone 308 as a function of time.

FIG. 4 shows a plot of the resonant frequency of the target zone 308 as a function of time. The x-axis 400 is the time axis. The axis 402 is the resonant frequency of molecules. The arrow labeled 404 indicates the period of the frequency oscillation. The period 404 is set to the ultrasound frequency. The points 406 correspond to points of maximum frequency these correspond to the first position 312 in FIG. 3. The points labeled 408 correspond to the minimum frequency and correspond to the second position 314 in FIG. 3. The arrow 410 indicates the magnitude or amplitude.

Figure 5:
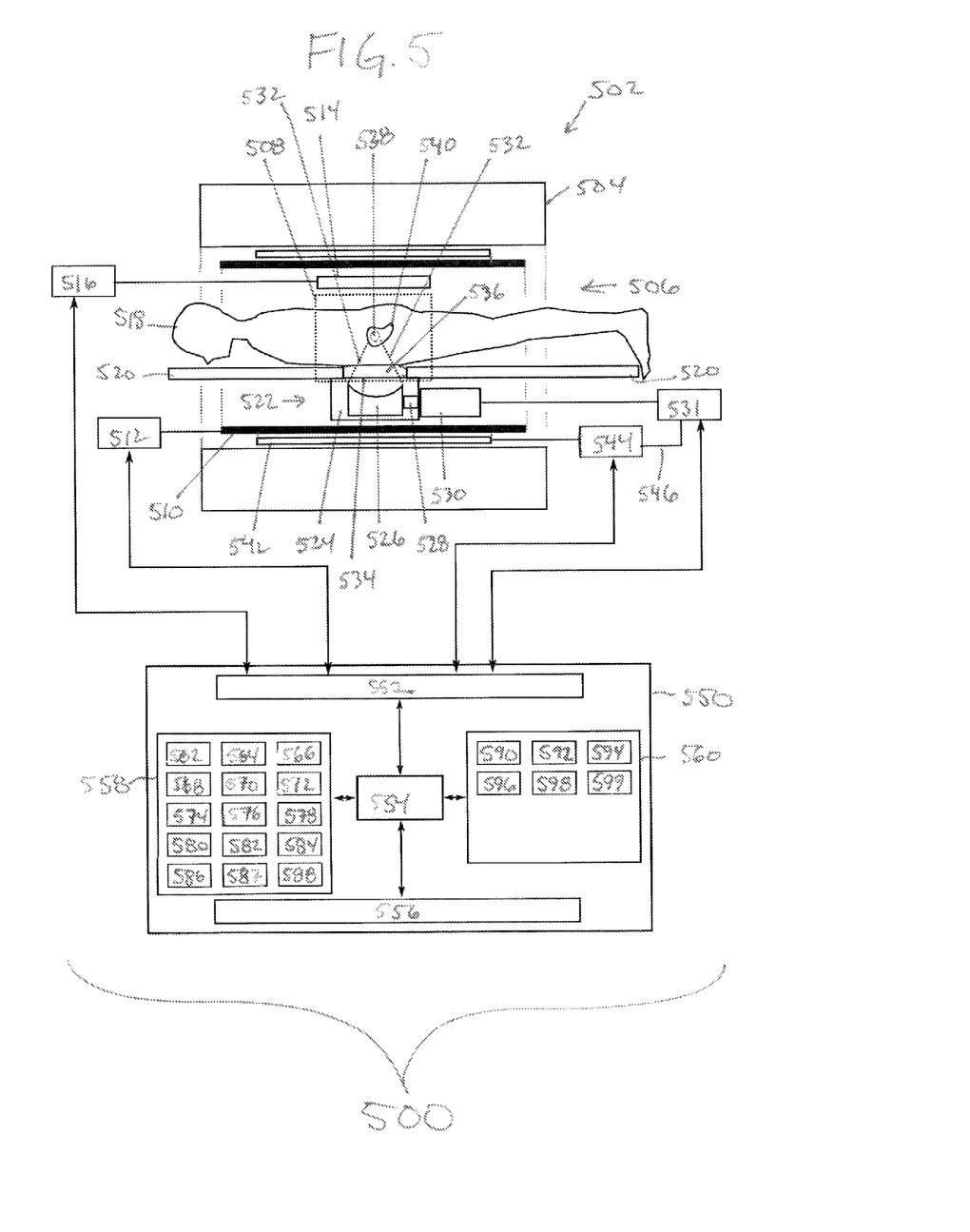
FIG. 5 illustrates an apparatus according to an embodiment of the invention.

FIG. 5 illustrates an apparatus 500 according to an embodiment of the invention. The apparatus 500 comprises a magnetic resonance imaging system 502. The magnetic resonance imaging system 502 comprises a magnet 504. The magnet 504 is a cylindrical type superconducting magnet and has a bore 506 through it. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 506 of the cylindrical magnet 504 there is a data acquisition zone 508 where the magnetic field is strong and uniform enough to perform magnetic resonance imaging.

Within the bore 506 of the magnet there are also a magnetic field gradient coils 542 which are used for acquisition of magnetic resonance data to spatially encode magnetic spins within a data acquisition zone 508 of the magnet 504. The magnetic field gradient coils 510 are connected to a magnetic field gradient coil power supply 512. The magnetic field gradient coils 510 are intended to be representative. Typically magnetic field gradient coils contain three separate sets of coils for spatially encoding in three orthogonal spatial directions. A magnetic field gradient power supply 512 supplies current to the magnetic field gradient coils. The current supplied to the magnetic field coils is controlled as a function of time and may be ramped or pulsed.

Adjacent to the data acquisition zone 508 is a radio-frequency coil 514 for manipulating the orientations of magnetic spins within the data acquisition zone 508 and for receiving radio transmissions from spins also within the data acquisition zone 508. The radio-frequency coil 514 may contain multiple coil elements. The radio-frequency coil 514 may also be referred to as a channel or antenna. The radio-frequency coil 514 is connected to a radio-frequency transceiver 516. The radio-frequency coil 514 and radio-frequency transceiver 516 may be replaced by separate transmit and receive coils and a separate transmitter and receiver. It is understood that the radio-frequency coil 514 and the radio-frequency transceiver 516 are representative. The radio-frequency coil 514 is intended to also represent a dedicated transmit antenna and a dedicated receive antenna. Likewise the transceiver 516 may also represent a separate transmitter and receivers. There is a subject 518 reposing on a subject support 520 within the bore 506 of the magnet 504.

The medical apparatus 500 further comprises a high-intensity focused ultrasound system 522. The high-intensity focused ultrasound system comprises a fluid-filled chamber 524. Within the fluid-filled chamber 524 is an ultrasound transducer 526. Although it is not shown in this Fig. the ultrasound transducer 526 may comprise multiple ultrasound transducer elements each capable of generating an individual beam of ultrasound. This may be used to steer the location of a sonication point 538 electronically by controlling the phase and/or amplitude of alternating electrical current supplied to each of the ultrasound transducer elements. The sonication point 538 is also referred to as the target zone 538.

The ultrasound transducer 526 is connected to a mechanism 528 which allows the ultrasound transducer 526 to be repositioned mechanically. The mechanism 528 is connected to a mechanical actuator 530 which is adapted for actuating the mechanism 528. The mechanical actuator 530 is shown as being connected to an ultrasound power supply 531 which supplies electrical power to the ultrasound transducer 526. In some embodiments the power supply may control the phase and/or amplitude of electrical power to individual ultrasound transducer elements. In some embodiments the mechanical actuator 530 is located outside of the bore 524 of the magnet 522.

The ultrasound transducer 526 generates ultrasound which is shown as following the path 532. The ultrasound 532 goes through the fluid-filled chamber 528 and through an ultrasound window 534. In this embodiment the ultrasound then passes through a gel pad 536. The gel pad is not necessarily present in all embodiments but in this embodiment there is a recess in the subject support 534 for receiving a gel pad 536. The gel pad 536 helps couple ultrasonic power between the transducer 526 and the subject 532. After passing through the gel pad 536 the ultrasound 532 passes through the subject 532 and is focused to a sonication point 538. The sonication point 538 is being focused within a target zone 530. The sonication point 538 may be moved through a combination of mechanically positioning the ultrasonic transducer 526 and electronically steering the position of the sonication point 538 to treat an entire treatment zone 540.

Also within the bore 506 of the magnet is a B0 field modulation coil 542. The B0 field modulation coil 542 is a coil which is used to generate a magnetic field to modulate the B0 field within the bore 506 of the magnet 504. The B0 field modulation coil 542 is connected to a B0 field modulation coil power supply 544. There is a connection 546 between the B0 field modulation coil power supply and the ultrasound power supply 531. This allows the phase of the B0 modulation relative to the generated ultrasound 532 to be controlled.

The magnetic field gradient coil power supply 512, the transceiver, the ultrasound power supply 531, and B0 field modulation coil power supply 544 are connected to a hardware interface 552 of computer system 550. The computer system 550 further comprises a processor 554 connected to the hardware interface 552, a user interface 556, computer storage 558, and computer memory 560.

The computer storage 558 is shown as containing first gradient commands 562 and second gradient commands 564. The computer storage 558 is further shown as containing ultrasound commands 566. The ultrasound commands 566 are commands used for controlling the high-intensity focused ultrasound system 522. The computer storage 558 is further shown as containing a set of phases 568. The computer storage 558 is further shown as containing a phase 570. The phase 570 is a phase determined using the set of phases 568 which determines the phase of an ultrasound beam in the target zone 538. The computer storage 558 is further shown as containing a set of frequency modulation magnitudes 572. The computer storage 558 is further shown as containing a maximizing magnitude 574. The maximizing magnitude 574 was determined using the set of frequency modulation magnitudes 572. The computer storage 558 is further shown as containing a set of directions 578. The computer storage is further shown as containing a first direction 580 determined using the set of directions 578. The first direction 580, the ultrasound amplitude 576 and the phase 570 are descriptive of an ultrasound beam traveling through the target zone 538.

The computer storage 558 is further shown as containing a set of control phases 582 and a set of corrected phases 584. The control phases 582 and the corrected phases 584 are phases for electronically steering the position of the target or sonication zone 538 of the ultrasonic transducer 526. The computer storage 558 is further shown as containing a treatment plan 586. The treatment plan 586 contains a description of the anatomy of the subject 518 and is useful for identifying the treatment zone 540. The computer storage 558 is further shown as containing magnetic resonance data 587 acquired using the magnetic resonance imaging system 502. The computer storage 558 is further shown as containing a magnetic resonance image 588. The magnetic resonance image 588 was reconstructed from the magnetic resonance data 587.

The computer memory 560 is shown as containing a control module 590. The control module contains computer executable code for controlling the operation and function of the apparatus 500. The computer memory 560 is further shown as containing an ultrasound command generation module 590. The ultrasound command generation module 590 contains computer executable code which was used for generating the first gradient commands 562 and the second gradient commands 564. The computer storage 560 further contains a set generation module 594. The set generation module 594 contains computer executable code which was used for generating the phases 568, the set of frequency modulation magnitudes 572 and the set of directions 578. The computer memory 560 is further shown as containing a control phase generation module 596. The control phase generation module 596 was used to generate the control phases 582 and the corrected phases 584. The computer memory 560 is further shown as containing an image reconstruction module 598. The image reconstruction module 598 contains computer executable code which is used for reconstructing the magnetic resonance image 588 from the magnetic resonance data 587. The computer memory 560 is further shown as containing an ultrasound command generation module 599. The ultrasound command generation module 599 contains computer executable code which is used for generating the ultrasound commands 566. In other embodiments the ultrasound command generation module 599 may also use the magnetic resonance image 588 and/or the treatment plan 586 to generate the ultrasound commands 566.

Figure 6:
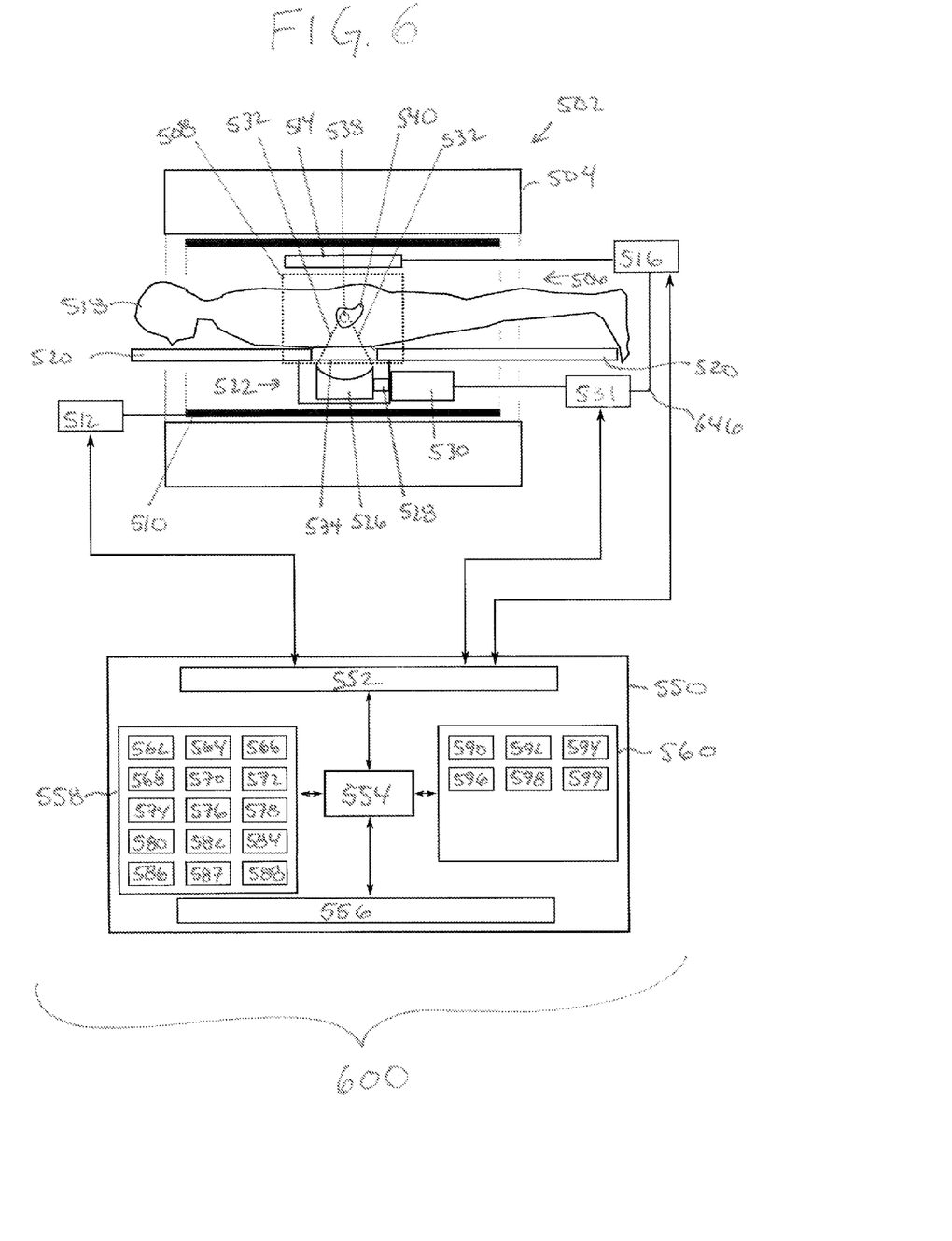
FIG. 6 illustrates an apparatus according to a further embodiment of the invention.

FIG. 6 shows an apparatus 600 very similar to that shown in FIG. 5. The difference between FIG. 6 and FIG. 5 is that in FIG. 6 there is no B0 field modulation coil or B0 field modulation coil power supply. Instead the transceiver 516 functions as the resonant frequency modulator. The transceiver 516 modulates frequency bursts at the ultrasound frequency. There is a connection 646 between the ultrasound power supply 531 and the transceiver 516. The connection 646 allows the phase of the RF modulation to be controlled relative to the ultrasound phase. The functioning of the computer system 550 and the data and instructions stored within the computer storage 558 and computer memory 560 are equivalent to that as is shown in FIG. 5.

Figure 7:
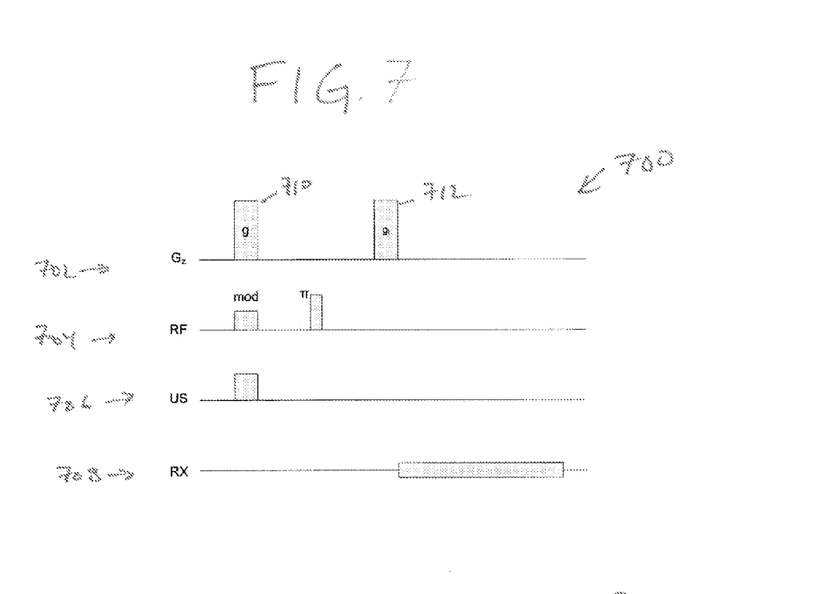
FIG. 7 shows a pulse sequence diagram which details a pulse sequence according to an embodiment of the invention.
Figure 8:
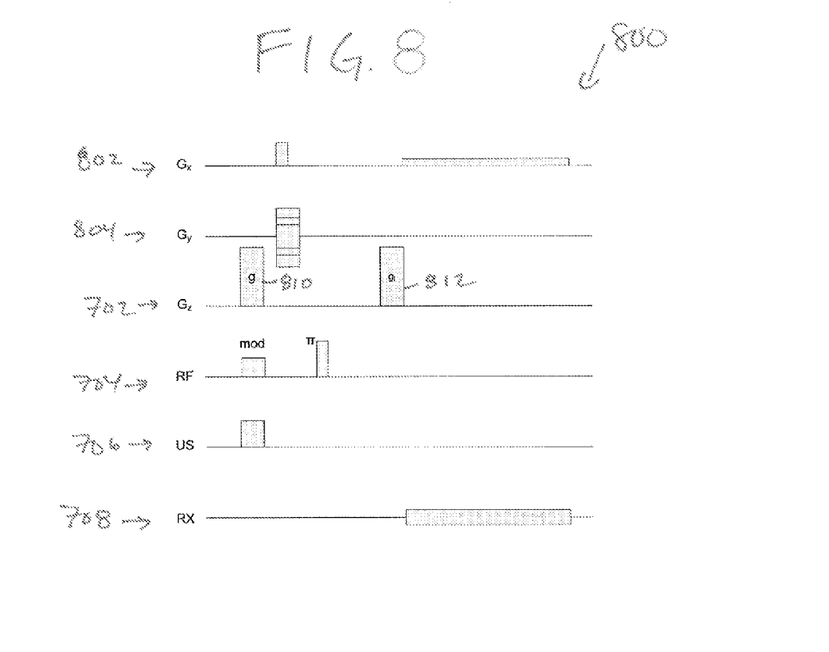
FIG. 8 shows a pulse sequence diagram which details a pulse sequence according to a further embodiment of the invention.

FIGS. 7 and 8 show pulse sequences which may be used to control the magnetic resonance imaging system according to an embodiment of the invention. These pulse sequences may for instance be stored in the computer storage 558 and/or computer memory 560. They may be used by the control module 590 to generate control signals for controlling the function and operation of the magnetic resonance imaging system 502.

In FIG. 7 the pulse sequence is designed for acquiring data from a voxel along the z-direction. In this example the z-gradient is directed along the same direction as the ultrasound. Bar 702 shows action by the z-gradient 704 shows RF transmissions by the transceiver. Bar 706 indicates when ultrasound is transmitted by the ultrasound transducer element. Bar 708 indicates when magnetic resonance data is received. The first 710 and second 712 gradient magnetic fields are shown on bar 702.

The pulse sequence in FIG. 8 is similar to that of FIG. 7 except this is designed for carrying multiple slices of data. In addition to the features shown in FIG. 7 there is a bar indicating the x-gradient 802 and the y-gradient 804.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 300 ultrasound transducer element
302 ultrasonic beam
304 first direction
306 B0 field
308 target zone of subject in equilibrium position
310 direction of travel
312 target zone of subject in first position
314 target zone of subject in second position
400 time axis
402 resonant frequency of molecules
404 period
406 maximum frequency
408 minimum frequency
410 magnitude or amplitude
500 apparatus
502 magnetic resonance imaging system
504 magnet
506 bore of magnet
508 data acquisition zone
510 magnetic field gradient coils
512 magnetic field gradient coil power supply
514 radio frequency coil
516 transceiver
518 subject
520 subject support
522 high intensity focused ultrasound system
524 fluid filled chamber
526 ultrasound transducer
528 mechanism
530 mechanical actuator
531 ultrasound power supply (add description to text)
532 path of ultrasound
534 ultrasound window
536 gel pad
538 target zone
540 treatment zone
542 B0 field modulation coil
544 B0 field modulation coil power supply
546 connection
550 computer
552 hardware interface
554 processor
556 user interface
558 computer storage
560 computer memory
562 first gradient commands
564 second gradient commands
566 ultrasound commands
568 set of phases
570 phase
572 set of frequency modulation magnitudes
574 maximizing magnitude
576 ultrasound amplitude
578 set of directions
580 first direction
582 control phases
584 corrected phases
586 treatment plan
587 magnetic resonance data
588 magnetic resonance image
590 control module 592 gradient command generation module
594 set generation module
596 control phase generation module
598 image reconstruction module
599 ultrasound command generation module
600 apparatus
646 connection
700 pulse sequence
702 z-gradient
704 RF
706 ultrasound
708 receive
710 first gradient magnetic field
712 second gradient magnetic field
800 pulse sequence
802 x-gradient
804 y-gradient
810 first gradient magnetic field
812 second gradient magnetic field

The invention claimed is:

1. An apparatus comprising:
a magnetic resonance imaging system configured to image a subject in an examination zone, the magnetic resonance imaging system including gradient magnetic coils configured to generate gradient magnetic fields in the examination zone, a modulator configured to modulate the gradient magnetic fields, an RF coil, and a memory carrying machine executable instructions;
an ultrasonic transducer configured to transmit an ultrasound beam along an ultrasound beam direction into a target zone of a subject, wherein the ultrasound beam has an ultrasound frequency and wherein the target zone of the subject is in the examination zone of the magnetic resonance system; and
at least one processor configured to execute the machine executable instructions to:
concurrently control the ultrasound transducer to transmit the ultrasound beam and the modulator of the magnetic resonance system to modulate gradient magnetic fields generated by a gradient magnetic field coils with the ultrasound frequency,
generate a set of phases;
control the modulator to modulate the gradient magnetic fields at the ultrasound frequency using each phase of the set of phases during repeated application of the gradient magnetic field,
determine a magnetic resonance signal from the target zone for each phase of the set of phases,
determine a phase of the set of phases which maximizes the magnetic resonance signal,
store the determined phase which maximizes the magnetic resonance signal in the memory, and
control the magnetic resonance imaging system to generate a magnetic resonance image with the gradient magnetic field modulated at the ultrasound frequency with the determined phase which maximizes the magnetic resonance signal each time the ultrasound beam is being transmitted.

2. An apparatus comprising:
a magnetic resonance imaging system configured to image a subject in an examination zone, the magnetic resonance imaging system including gradient magnetic coils configured to generate gradient magnetic fields in the examination zone, a transceiver configured to modulate the gradient magnetic fields, an RF coil, and a memory carrying machine executable instructions;
an ultrasonic transducer configured to transmit an ultrasound beam along an ultrasound beam direction into a target zone of a subject, wherein the ultrasound beam has an ultrasound frequency and wherein the target zone of the subject is in the examination zone of the magnetic resonance system; and
at least one processor configured to execute the machine executable instructions to:
concurrently control the ultrasound transducer to transmit the ultrasound beam and the transceiver of the magnetic resonance system to modulate gradient magnetic fields generated by a gradient magnetic field coils with the ultrasound frequency,
generate a set of frequency modulation magnitudes;
control the transceiver to modulate the gradient magnetic fields in the target zone at the ultrasound frequency using each frequency modulation magnitude of the set of frequency modulation magnitudes during repeated application of the gradient magnetic field,
determine a magnetic resonance signal from the target zone for each magnitude of the set of frequency modulation magnitudes,
determine a maximizing magnitude using the set of frequency modulation magnitudes which caused the largest magnetic resonance signal from the target zone,
store the maximizing magnitude in the memory, and
control the magnetic resonance imaging system to generate a magnetic resonance image modulating the gradient magnetic field at the ultrasound frequency with the stored maximizing magnitude when the ultrasound beam is transmitted.

3. The apparatus of claim 2, wherein the at least one processor is configured to calculate an ultrasound beam amplitude for the target zone using the maximizing magnitude.

4. An apparatus comprising:
a magnetic resonance imaging system configured to image a subject in an examination zone, the magnetic resonance imaging system including gradient magnetic coils configured to generate gradient magnetic fields in the examination zone, a transceiver configured to modulate the gradient magnetic fields, an RF coil, and a memory carrying machine executable instructions;
an ultrasonic transducer configured to transmit an ultrasound beam along an ultrasound beam direction into a target zone of a subject, wherein the ultrasound beam has an ultrasound frequency and wherein the target zone of the subject is in the examination zone of the magnetic resonance system; and
at least one processor configured to execute the machine executable instructions to:
concurrently control the ultrasound transducer to transmit the ultrasound beam and the transceiver to modulate gradient magnetic fields generated by a gradient magnetic field with the ultrasound frequency,
generate a set of directions;
modulate the gradient magnetic field in the target zone at the ultrasound frequency using each direction of the set of directions during repeated application of the gradient magnetic field;
determine a magnetic resonance signal from the target zone for each direction of the set of directions;
determine the ultrasound beam direction using the magnetic resonance signal from the target zone, the ultrasound beam direction being one of the set of directions which maximizes the magnetic resonance signal from the target zone;

store the determined ultrasound beam direction which maximizes the magnetic resonance signal in the memory; and control the magnetic resonance imaging system to generate a magnetic resonance image modulating the gradient magnetic field at the ultrasound frequency in the stored ultrasound beam direction.

5. A method of operating a magnetic resonance imaging apparatus, the method comprising:

with one or more processors executing machine executable instructions to control a magnetic field gradient coil of the magnetic resonance imaging apparatus to generate gradient magnetic fields through a target zone, wherein the target zone is a portion of a subject into which an ultrasonic beam is transmitted in an ultrasonic beam direction and wherein the gradient magnetic fields have a gradient direction parallel to the ultrasound beam direction;

with the one or more processors executing machine executable instructions to control the magnetic field gradient coil to modulate the gradient magnetic fields at the ultrasound frequency during transmission of the ultrasonic beam;

with the one or more processors executing machine executable instructions to control the magnetic field gradient coil to generate opposite polarity gradient magnetic fields through the target zone prior to the acquisition of the magnetic resonance data, wherein the opposite polarity gradient magnetic fields have a polarity opposite to that of the gradient magnetic field applied during ultrasound beam transmission;

controlling a radio frequency coil to apply a radio frequency inversion pulse between the transmission and opposite polarity gradient magnetic fields;

acquiring magnetic resonance signal from the target zone;

wherein the method further includes:

with the one or more processors executing machine executable instructions to control the magnetic field gradient coils to repeatedly modulate the gradient magnetic fields during transmission of the ultrasound beam at each phase of a set of phases or each frequency of a set of frequencies;

with the one or more processors executing machine executable instructions to determine which phase of the set of phases or which frequency of the set of frequencies maximizes the magnetic resonance signals;

with the one or more processors executing machine executable instructions to repeatedly acquire the magnetic resonance signal with the gradient magnetic field modulated with the determined phase or frequency which maximizes the magnetic resonance signal; and with the one or more processors executing machine executable instructions to reconstruct the repeatedly acquired magnetic resonance signals into a magnetic resonance image.

6. A non-transitory computer readable storage medium including a set of instructions for execution by one or more processors of an magnetic resonance apparatus to control the magnetic resonance apparatus to perform the method of claim 5.

* * * * *